United States Patent [19]
Herold et al.

[11] Patent Number: 6,159,005
[45] Date of Patent: Dec. 12, 2000

[54] PHOTOPOLYMERIZATION APPARATUS

[75] Inventors: Wolf-Dietrich Herold, Seefeld; Ralf Kuerschner, Gauting; Peter Koran, Weilheim, all of Germany

[73] Assignee: Espe Dental AG, Seefeld, Germany

[21] Appl. No.: 09/079,266

[22] Filed: May 15, 1998

[30] Foreign Application Priority Data

May 26, 1997 [DE] Germany .................. 297 09 228 U

[51] Int. Cl.$^7$ ...................................................... A61C 1/00
[52] U.S. Cl. ............................................................ 433/29
[58] Field of Search .................... 433/29; 606/3, 606/13, 16, 17; 257/13

[56] References Cited

U.S. PATENT DOCUMENTS

| | | | |
|---|---|---|---|
| 4,826,431 | 5/1989 | Fujimura et al. | 433/29 |
| 5,267,252 | 11/1993 | Amano | 257/13 |
| 5,388,987 | 2/1995 | Badoz et al. | 433/29 |
| 5,554,029 | 9/1996 | Kowalyk et al. | 433/29 |
| 5,578,839 | 11/1996 | Nakamura et al. | 257/13 |
| 5,610,413 | 3/1997 | Fan et al. | 257/97 |
| 5,634,711 | 6/1997 | Kennedy et al. | 362/119 |
| 5,711,665 | 1/1998 | Adam et al. | 433/29 |
| 5,751,013 | 5/1998 | Kidoguchi et al. | 257/13 |
| 6,005,258 | 12/1999 | Manabe et al. | 257/13 |

FOREIGN PATENT DOCUMENTS

| | | | |
|---|---|---|---|
| 581750 | 2/1994 | European Pat. Off. | 433/29 |
| 38 40 984 | 6/1990 | Germany . | |
| 42 11 230 | 10/1993 | Germany . | |

*Primary Examiner*—Todd E. Manahan
*Attorney, Agent, or Firm*—Foley & Lardner

[57] ABSTRACT

An apparatus for photopolymerizing synthetic materials, specifically dental materials containing camphor quinone or phosphine oxide as a photo-initiator, includes a light source constituted by a semiconductor base solid-state radiation emitter 12 which emits in the blue spectral range. Since the radiation emitter emits in a small useful spectral range only, any heat radiation is avoided. The overall device is formed as a small, light-weight and handy device with a built-in battery 15. The solid-state radiation emitter 12, which is preferably operated in the light emitting diode (LED) mode, may be arranged directly on the tip 20 of the apparatus which can be directed toward the treatment site.

11 Claims, 1 Drawing Sheet

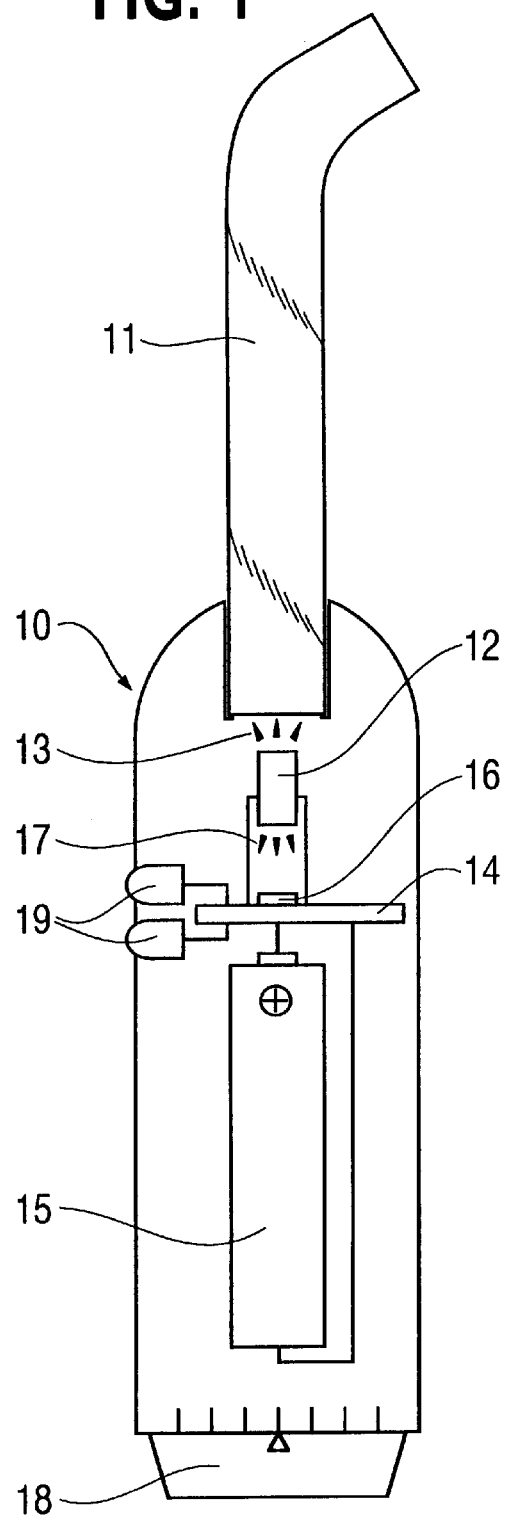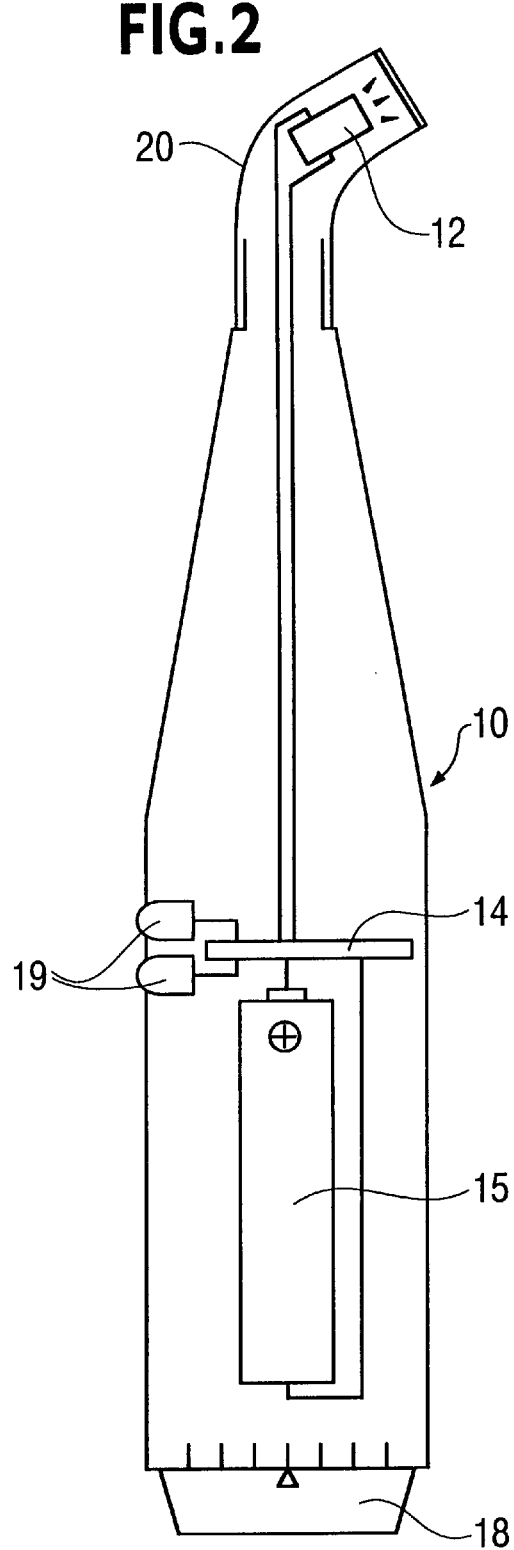

PHOTOPOLYMERIZATION APPARATUS

BACKGROUND OF THE INVENTION

In the dental technology, a plurality of synthetic materials, so-called composites, are known which polymerize due to a metacrylate based curing mechanism when irradiated with light. As the essential photo-initiator these materials contain camphor quinone or phosphine oxide which absorbs a broad band within the blue spectral range, with an absorption maximum at about 472 nm and 430 nm, respectively.

Depending on the color of the material, the polymerization reaction requires light having an intensity of at least 1 to 5 $mW/cm^2$ within a very thin layer. In the practice of polymerizing tooth stoppings or dental replacement parts, a light intensity of at least 250 $mW/cm^2$ is required within an appropriate period of time to achieve polymerization of sufficient degree and depth. Commercially available dental polymerization apparatus emit light at an intensity of about 400 to 500 $mW/cm^2$, sometimes up to 700 $mW/cm^2$.

Desk apparatus are known in which the light is generated and focused within the apparatus and transmitted to the treatment site within the patient's mouth by means of a flexible optical waveguide having a length of typically 1.5 to 2 m. In addition to a substantial loss of light that occurs at its input and output faces, such an optical waveguide usually has a diameter of about 10 to 15 mm and is therefore relatively stiff and unwieldy.

In other prior-art apparatus, such as known from, e.g., German Offenlegungsschrift No. 3,840,984, the light is generated and focused within a gun-shaped hand piece and transmitted to the treatment site by means of a rigid light conducting rod made of fibers or quartz. A chief disadvantage of these apparatus results from a considerable heating of the hand piece and, as that is held close to the treatment site, of the irradiated location itself. Moreover, the power supply cable required in this type of apparatus for feeding current to the hand piece is considered troublesome.

German Offenlegungsschrift No. 4,211,230 discloses a battery-powered apparatus which is independent of the mains or a power supply unit but requires comparatively large and heavy batteries to provide the necessary high electric output, and is thus difficult to handle.

The known photopolymerization apparatus often employ tungsten-halogen lamps which emit light in a comparatively wide spectral range, thus output the largest portion of their energy as heat and light in the red and green wavelength ranges. Only about 2 percent of the power input is emitted in a spectral range of about 400 to 515 nm, which is the range useful for the above-mentioned composite materials using camphor quinone or phosphine oxide as a photo-initiator.

Conventionally employed light sources have the further difficulty that their light output decays throughout their life in a manner that is not readily detected by the user, so that the quality of the polymerization deteriorates with time.

Another disadvantage resides in the fact that optical components such as lenses and reflectors are required in order suitably to image the helix of the lamp to the entry end of the waveguide and illuminate the full area of the entry end without losing light energy. Also, filters are needed to absorb the heat radiation and to reduce the halogen light of the desired spectral range. These optical components may also reduce the light output due to ageing and defects, thereby rendering a safe polymerization impossible.

It is a further disadvantage of known apparatus, specifically hand-held apparatus, that air circulation required for the removal of heat also causes a spreading of bacteria. Due to their open design, as is necessary for ventilation, and due to their size, these apparatus are difficult to sterilize and disinfect.

SUMMARY OF THE INVENTION

It is a general object of the invention to avoid at least some of the disadvantages encountered with comparable prior-art apparatus. As a more specific object of the invention, an apparatus for the photopolymerizing synthetic materials, specifically dental materials using camphor quinone or phosphine oxide as a photo-initiator, is to be provided which generates light in the useful blue spectral range with maximum efficiency.

This object is met by an apparatus for photopolymerizing synthetic materials, specifically dental materials containing photo-initiators, including a light source for emitting light in the blue spectral range, wherein the light source is a solid-state radiation emitter on the basis of a semiconductor composed of elements of the main groups III and V of the Periodic Table.

The use of this type of solid-state radiation emitter in a polymerization apparatus, specifically in a dental polymerization apparatus, results in the following advantages:

(1) Since the light emission is limited to a defined wavelength range, in this case the blue range, no additional heat is generated. Accordingly, the apparatus requires no ventilator and may thus be designed as a closed, encapsulated device that can be sterilized as a whole.

(2) The fact that any heat generation is avoided, is advantageous also for the polymerization process itself because shrinkage of the synthetic material caused by heating and cooling and the danger of boundary gaps resulting therefrom are avoided.

(3) While the light output of solid-state radiation emittters varies over time, this effect may be compensatted by simply adjusting the diode current so as to correct the light output. Since laser diodes emit two opposite beams of light, it is generally possible to use one of these beams as the useful beam for the polymerization and the other as a reference beam for controlling the intensity of the useful beam.

(4) Due to the fact that the solid-state radiation emitter emits light in a small useful spectral range only, it requires little power to achieve radiation of sufficient intensity. Therefore, the apparatus may be readily powered by a built-in-battery, thereby avoiding optical waveguides or power supply cables as required in known devices.

(5) The small size of the solid-state radiation emitter in connection with the absence of any heat generation results in an apparatus which may be of a small, light-weight and handy design.

(6) Since the generation of light is virtually free of inertia, pulsed operation is possible to achieve very high intensities for short periods. This results in an increased transparently of the material to be polymerized, because all absorption levels of the material can be occupied due to the high quantity of photons.

(7) Other than with conventional lasers, the divergent elliptical radiation characteristic of laser diodes makes the use of optical components for optimum irradiation of the wave guide unnecessary.

In a preferred embodiment, the semiconductor is based on gallium nitride containing suitable ternary additives.

When the solid-state radiation emitter is operated in the LED mode, there is the advantage of a two-dimensional radiation in a bandwidth that is not excessively small. Both features are specifically advantageous for dental applications because a larger radiating surface is closer to the usual dimensions of tooth surfaces to be irradiated and because the larger spectral width corresponds more closely to the absorption band width of the molecules which initiate the polymerization. All this contributes to an efficient polymerization.

Alternatively, a particularly intensive beam of light is achieved when the solid-state radiation emitter is operated in the laser mode.

Due to its small size, the solid-state radiation emitter may be disposed directly on the tip of a polymerization apparatus which may be directed toward the treatment site. This results in the advantage of specifically low radiation loss.

Alternatively, the solid-state radiation emitter may be disposed at the light entry end of an optical waveguide which may be directed toward the treatment site. In this embodiment, in which the radiation emitter is disposed inside the apparatus, the absence of any heat generation again allows the apparatus to be made extremely small and handy.

In another embodiment, the apparatus may include a rechargeable or non-rechargeable battery for powering the solid-state radiation emitter.

The solid-state radiation emitter is preferably a laser diode which emits a forward beam used for the polymerization proper and a backward beam used as a reference beam for controlling the intensity of the polymerization beam.

In accordance with a further embodiment of the invention, the solid-state radiation emitter is pulsed, which permits a substantially higher intensity and, thereby, a deeper penetration of the light beam into the material to be polymerized.

The diode and the optical waveguide may be arranged in such a fixed mutual orientation that the use of a waveguide entry aperture which is geometrically adapted to the cross-section of the laser beam, preferably an elliptical aperture, allows the useful beam to be completely imaged onto the entry end of the waveguide.

BRIEF DESCRIPTION OF THE DRAWING

The invention will now be explained in more detail with reference to the accompanying drawing, in which FIGS. 1 and 2 illustrate two photopolymerization apparatus embodying the invention.

DETAILED DESCRIPTION OF PREFERRED EMBODIMENTS

The apparatus of FIG. 1 consists of a hand piece 10 with a light conducting rod 11 having its entry end inserted into the front end of the hand piece. The light spill end of the light conducting rod 11 is curved for easier handling.

The light entry end of the rod 11 receives the useful beam emitted by a solid-state radiation emitter 12, which is a light emitting diode composed of elements of the main groups III and V of the Periodic Table, preferably gallium nitride, emitting in the blue spectral range. The diode is preferably operated in a pulse mode. For adaptation to the elliptical cross-section of the useful beam 13, the entry end of the light conducting rod 11 also has an elliptical cross-section.

The hand piece 10 further comprises a printed circuit board 14 with an integrated circuit for controlling the solid-state radiation emitter 12 and a battery 15 for power supply.

Disposed on the circuit board 14 and connected to the integrated circuit is a sensor 16 which receives the beam 17 emitted from the reverse side of the light emitting diode 12 as a reference beam for controlling the light output of the diode 12 and thus the energy of the useful beam 13.

At the end remote from the light conducting rod 11, the hand piece 10 is provided with a time control 18 in the form of a rotary knob. Two light emitting diodes 19 of low radiation output are arranged on a side of the hand piece 10 for optically displaying the operating condition.

The light conducting rod 11 may be rotatable with respect to the hand piece 10 so that the light spill end can be rotated to assume the most convenient position with respect to the location to be irradiated without requiring a change in the position of the hand piece 10 and thus of the time control 18 and the display diodes 19.

The apparatus of FIG. 2 differs from that of FIG. 1 in that the solid-state radiation emitter 12 is disposed directly on the tip portion 20 of the hand piece 10. The tip portion 20, which contains the radiation emitter 12, is curved similar to the light spill end of the light conducting rod 11 of FIG. 1, and is rotatable with respect to the hand piece 10 so that the most convenient position relative to the treatment site may be achieved without changing the position of the hand piece 10 itself.

What is claimed is:

1. An apparatus for photopolymerizing synthetic materials containing photo-initiators, said apparatus comprising a light source for emitting light in the blue spectral range, said light source being a solid-state radiation emitter on the basis of a semiconductor composed of elements of the main groups III and V of the Periodic Table, wherein said radiation emitter is a laser diode emitting a forward beam used for polymerization and a backward beam used as a reference beam for controlling the intensity of said forward beam.

2. The apparatus of claim 1, wherein said semiconductor is made of gallium nitride.

3. The apparatus of claim 1, wherein said radiation emitter includes an LED.

4. The apparatus of claim 1, wherein said radiation emitter includes a laser.

5. The apparatus of claim 1, further comprising a tip portion adapted to be directed to a treatment site, wherein said radiation emitter is disposed directly on said tip portion.

6. The apparatus of claim 1, further comprising an optical waveguide having a spill end adapted to be directed toward a treatment site, and a light entry end, wherein said radiation emitter is disposed at said light entry end.

7. The apparatus of claim 6, wherein said optical waveguide and said radiation emitter are arranged in a fixed mutual orientation, and the entry end of said optical waveguide has an aperture sized and dimensioned in accordance with the cross-section of the beam emitted by said radiation emitter.

8. The apparatus of claim 7, wherein said aperture of said entry end is elliptical.

9. The apparatus of claim 1, further comprising a battery for supplying energy to said radiation emitter.

10. The apparatus of claim 9, wherein said battery is a rechargeable battery.

11. The apparatus of claim 1, wherein radiation emitter outputs pulses of radiation.

\* \* \* \* \*